US008288535B2

(12) United States Patent
Fujita et al.

(10) Patent No.: US 8,288,535 B2
(45) Date of Patent: Oct. 16, 2012

(54) SYNTHESIS METHOD OF POLYMER COMPLEX CRYSTAL

(75) Inventors: Makoto Fujita, Chiba (JP); Masaki Kawano, Chiba (JP); Tsuyoshi Haneda, Tokyo-to (JP); Kiyoshi Nakanishi, Susono (JP); Takahiro Kojima, Tokyo-to (JP)

(73) Assignees: The University of Tokyo, Bunkyo-ku (JP); Toyota Jidosha Kabushiki Kaisha, Toyota-shi (JP)

( * ) Notice: Subject to any disclaimer, the term of this patent is extended or adjusted under 35 U.S.C. 154(b) by 470 days.

(21) Appl. No.: 12/530,240

(22) PCT Filed: Mar. 7, 2008

(86) PCT No.: PCT/JP2008/054696
§ 371 (c)(1),
(2), (4) Date: Nov. 2, 2009

(87) PCT Pub. No.: WO2008/111664
PCT Pub. Date: Sep. 18, 2008

(65) Prior Publication Data
US 2010/0105901 A1   Apr. 29, 2010

(30) Foreign Application Priority Data
Mar. 7, 2007  (JP) ............................... 2007-057611

(51) Int. Cl.
*C07F 3/06* (2006.01)
(52) U.S. Cl. ...................................................... 544/181
(58) Field of Classification Search ................... 544/181
See application file for complete search history.

(56) References Cited

U.S. PATENT DOCUMENTS

| 5,019,263 A | 5/1991 | Haag et al. |
| 2011/0098414 A1 | 4/2011 | Fujita et al. |

FOREIGN PATENT DOCUMENTS

| JP | 07185275 A | 7/1995 |
| JP | 08318141 A | 12/1996 |
| JP | 2001232156 A | 8/2001 |
| JP | 2002126512 A | 5/2002 |
| JP | 2003210950 A | 7/2003 |
| JP | 2005255545 A | 9/2005 |
| JP | 2006188560 A | 7/2006 |

OTHER PUBLICATIONS

Osamu Ohmori, Masaki Kawano, and Makoto Fujila, "Crystal-to-Crystal Guest Exchange of Large Organic Molecules within a 3D Coordination Network," Journal of the American Chemical Society, Dec. 22, 2004, vol. 126, 2 pages.

*Primary Examiner* — Charanjit Aulakh
(74) *Attorney, Agent, or Firm* — Gifford, Krass, Sprinkle, Anderson & Citkowski, P.C.

(57) ABSTRACT

Disclosed is a synthesis method for synthesizing in a short time and selectively a microcrystal of a polymer complex having three three-dimensionally and regularly arranged channels.
Specifically disclosed is a synthesis method of a polymer complex crystal wherein (1) a metallic solution, which is a mixture of zinc halide(II) and a solvent A that can dissolve the zinc halide, is mixed with (2) a ligand solution, which is a mixture of a tridentate ligand that has three coordination sites coordinated to zinc of the zinc halide and a solvent B that can dissolve the tridentate ligand, to be a single-phase solution, thereby synthesizing a microcrystal of a polymer complex having a three-dimensional coordination network formed by coordinating the tridentate ligand to the zinc and having channels that are three-dimensionally and regularly arranged in the three-dimensional coordination network.

6 Claims, 3 Drawing Sheets

Monoclinic *C2/c*
a / Å = 35.978   b / Å = 15.007
c / Å = 30.616   $\beta$ /° = 102.47
V / Å$^3$ = 16140.3   T / K = 105
Capillary $\phi$ / mm = 0.3

(1A)

(1B)

Monoclinic C2/c
a / Å = 35.25  b / Å = 14.704
c / Å = 30.97  β / ° = 103.04
V / Å³ = 15638.3  T / K = 300
Capillary φ / mm = 0.3

(2A)

(2B)

Monoclinic C2/c
a / Å = 36.370 (7), b / Å = 15.090 (3)
c / Å = 31.266 (6), β / ° = 103.78
V / Å³ = 16665.4, T / K = 193
$R_1$ = 9.94

(3A)

(3B)

SYNTHESIS METHOD OF POLYMER COMPLEX CRYSTAL

CROSS-REFERENCE TO RELATED APPLICATIONS

This application is the U.S. national phase of PCT/JP2008/054696 filed Mar. 7, 2008, which claims priority of Japanese Patent Application No. 2007-057611 filed Mar. 7, 2007.

TECHNICAL FIELD

The present invention relates to a method of synthesizing a crystal of a polymer complex having three-dimensionally and regularly arranged channels in a short time.

BACKGROUND ART

By allowing a mixture containing many kinds of compounds to be passed through, or in contact with, a material having a porous structure which takes a guest compound in, a specific compound can be selectively taken out. As such a microporous material, for example, a polymer complex having organic ligands complexed with a trans it ion metal, or zeolite is known and used in many applications as a selective reversible adsorbent, a catalyst carrier, etc.

SUMMARY OF INVENTION

Technical Problem

A common method of synthesizing a microporous polymer complex is a counter diffusion method in which a solution containing a metallic species is gently brought into contact with a solution containing a ligand so that the metallic species gradually reacts with the ligand at the interface of the solutions, thereby growing a crystal of a polymer complex slowly. Such crystal growth takes a long period of time such as one week or more. Therefore, although microporous polymer complexes have been expected to be used and applied for various purposes due to their high functionality, it has been difficult to practically use them for purposes where bulk synthesis is required.

In the research and development of microporous polymer complexes, the inventors of the present invention made a diligent study of the method of synthesizing microporous polymer complexes and the method of specifying the structure of polymer complexes. As a result, they have found out that contrary to their expectations, a single-component microcrystal of a polymer complex having three-dimensionally and regularly arranged channels can be synthesized without taking, unlike in the counter diffusion method, a long time to grow a crystal.

That is, an object of the present invention is to provide a synthesis method for synthesizing a microcrystal of a polymer complex having three-dimensionally and regularly arranged channels in a short time and selectively.

Solution to Problem

The synthesis method of the present invention is characterized by that (1) a metallic solution, which is a mixture of zinc halide (II) and a solvent A that can dissolve the zinc halide, is mixed with (2) a ligand solution, which is a mixture of a tridentate ligand that has three coordination sites coordinated to zinc of the zinc halide and a solvent B that can dissolve the tridentate ligand, to be a single-phase solution, thereby synthesizing a microcrystal of a polymer complex having a three-dimensional coordination network formed by coordinating the tridentate ligand to the zinc and having channels that are three-dimensionally and regularly arranged in the three-dimensional coordination network.

By mixing a nitrobenzene solution of 2,4,6-tris-(4-pyridyl)-1,3,5-triazine with a methanol solution of $ZnBr_2$ or $ZnI_2$ at room temperature and stirring the mixture for a short time, the inventors of the present invention has succeeded in obtaining a single-component microcrystalline powder (that is, having the same composition formula and isomorphic crystal structure) of a polymer complex in a much shorter time than that of the counter diffusion method, thereby completing the present invention.

According to the present invention, a crystal of a polymer complex having three-dimensionally and regularly arranged channels can be synthesized in a short time and in bulk quantity without taking a long time to grow a crystal unlike in the counter diffusion method, which is a conventional method of synthesizing a polymer complex.

The step of mixing (1) the metallic solution with (2) the ligand solution may be performed at room temperature.

Specific examples of the zinc halide (II) include zinc bromide ($ZnBr_2$), zinc iodide ($ZnI_2$).

Suitable examples of the tridentate ligand include one wherein the directions of coordination bonds formed by the three coordination sites thereof are present in almost the same plane, and one wherein the three coordination sites are arranged radially from the center of the tridentate ligand at regular intervals.

Specific examples of the tridentate ligand include an aromatic compound represented by the following Formula (1):

$$Ar\text{-}(X\text{---}Y)_3 \qquad \text{Formula 1}$$

wherein Ar is a structure having an aromatic ring; X is a divalent organic group or a single bond through which Ar and Y are directly bound to each other; Y is an atom having a coordination site or an atomic group having a coordination site; and a plurality of Xs contained in one molecule may be different from one another, and a plurality of Ys contained may be different from one another.

More specific example of the tridentate ligand include 2,4,6-tris-(4-pyridyl)-1,3,5-triazine.

As the solvent B, for example, there may be mentioned an aromatic compound, and specific examples of the aromatic compound include nitrobenzene.

Advantageous Effects of Invention

According to the present invention, a microcrystalline powder of a polymer complex having three-dimensionally and regularly arranged channels can be synthesized in a much shorter time than that of the counter diffusion method and in bulk quantity. That is, the present invention makes it possible to synthesize microporous polymer complexes in a short time and efficiently, which have been synthesized by taking a long period of time such as one week or more. Therefore, the present invention is highly productive. Furthermore, the present invention greatly contributes to practical application of polymer complexes which have been expected to be used in various fields.

DESCRIPTION OF EMBODIMENTS

The synthesis method of the present invention is characterized by that (1) a metallic solution, which is a mixture of zinc halide (II) and a solvent A that can dissolve the zinc halide, is mixed with (2) a ligand solution, which is a mixture of a tridentate ligand that has three coordination sites coordinated to zinc of the zinc halide and a solvent B that can dissolve the tridentate ligand, to be a single-phase solution, thereby synthesizing a microcrystal of a polymer complex having a three-dimensional coordination network formed by coordinating the tridentate ligand to the zinc and having channels that are three-dimensionally and regularly arranged in the three-dimensional coordination network.

Figure 3:
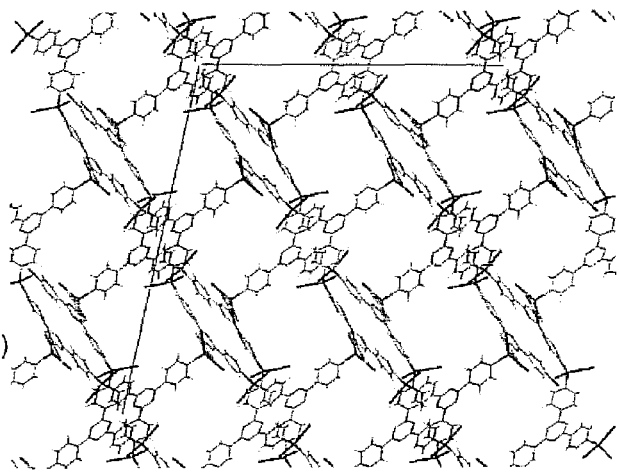
FIG. 3 shows diagrams showing the crystal structure of polymer complex 1'.
Figure 3:
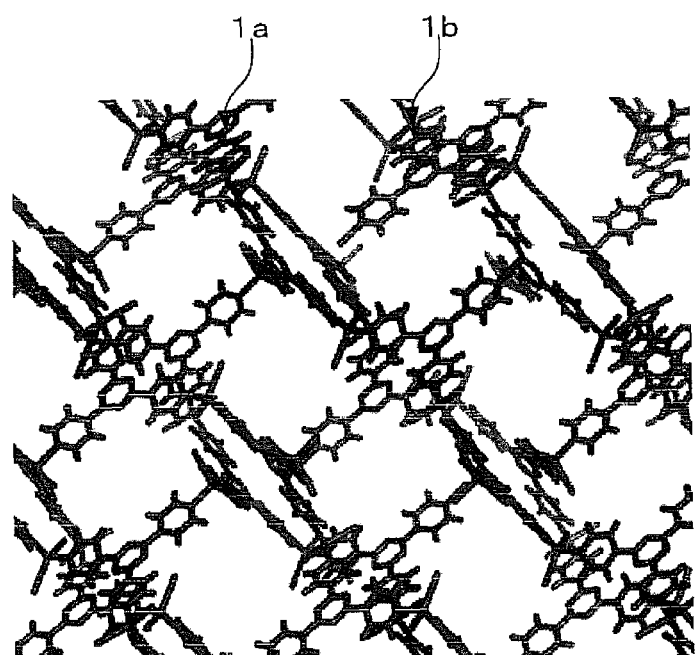

As a result of diligently studying the method of synthesizing a polymer complex and the method of specifying the structure of a polymer complex, the present inventors have found out that as shown in FIG. 1(A), a white powder obtained by mixing a nitrobenzene solution of 2,4,6-tris-(4-pyridyl)-1,3,5-triazine with a methanol solution of $ZnI_2$ at room temperature and stirring the mixture for 30 seconds to be a single-phase solution (seethe following Formula 5) consists of a single-component polymer complex having a complexed three-dimensional coordination network formed by interpenetration of three-dimensional coordination networks 1a and 1b each having a plurality of 2,4,6-tris-(4-pyridyl)-1, 3,5-triazine (hereinafter may be referred to as tpt) and $ZnI_2$ bound three-dimensionally to each other via coordinate bonding (see FIG. 3 (3B)).

More specifically, the inventors of the present invention have found out that this polymer complex has a composition represented by $[(ZnI_2)_3(tpt)_2(PhNO_2)_{5.5}]_n$. Furthermore, the inventors have found out that its three-dimensional structure is isomorphic to that of single crystal $[(ZnI_2)_3(tpt)_2(PhNO_2)_{5.5}]_n$ synthesized by some of the present inventors who also specified the structure of the single crystal, by crystal growing with a counter diffusion method using a nitrobenzene solution of tpt and a methanol solution of $ZnI_2$. That is, the three-dimensional structure is a monoporous network structure (see FIG. 3 and Angew. Chem. Int. Ed. 2002, 41, No. 18, pp. 3392-3395).

In addition, the inventors of the present invention have found out that polymer complex $[(ZnBr_2)_3(tpt)_2(PhNO_2)_5(H_2O)]_n$ which has a three-dimensional coordination network isomorphic to that of the single crystal $[(ZnI_2)_3(tpt)_2(PhNO_2)_{5.5}]_n$ can be obtained by using $ZnBr_2$ as the zinc halide, in place of the $ZnI_2$ (seethe following Formula (6)).

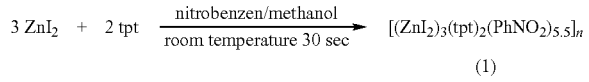

(Formula 5)

$3 ZnI_2 + 2 tpt \xrightarrow[\text{room temperature 30 sec}]{\text{nitrobenzen/methanol}} [(ZnI_2)_3(tpt)_2(PhNO_2)_{5.5}]_n$ (1)

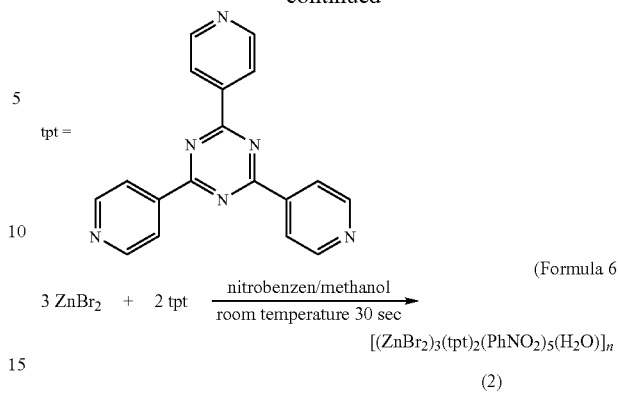

tpt =

(Formula 6)

$3 ZnBr_2 + 2 tpt \xrightarrow[\text{room temperature 30 sec}]{\text{nitrobenzen/methanol}} [(ZnBr_2)_3(tpt)_2(PhNO_2)_5(H_2O)]_n$ (2)

Conventionally, there has been established no method of specifying the structure of a polymer complex which has a three-dimensional coordination network and is obtained in the form of microcrystalline powder. However, the inventors of the present invention have made it possible to specify the higher-order structure (crystal structure) of powdery samples by using an analysis method such as powder X-ray structure analysis with radiation synchrotron followed by analysis of the resulting data with a software program such as RIETAN-FP and DASH, elemental analysis, and thermogravimetry-mass spectrometry (TG-MS). That is, it has been clarified by using the method which has been newly developed by the present inventors for analyzing the high-order structure of powder samples, that the powder obtained by the synthesis method of the present invention is microcrystals of a polymer complex having a three-dimensional coordination network.

The synthesis method of the present invention is to form a polymer complex having a three-dimensional coordination network in such a manner that a plurality of multidentate ligands having three or more coordination sites are instantly coordinated to tetrahedral metal species serving as a clasp to connect the multidentate ligands by mixing them to be a single-phase in the presence of a template solvent which serves as a template of channels, followed by self-organization of the multidentate ligands and tetrahedral metal species.

Unlike the counter diffusion method, the synthesis method of the present invention conducts synthesis by mixing the above-mentioned components constituting a polymer complex for a short time to be a single-phase. $[(ZnI_2)_3(tpt)_2(PhNO_2)_{5.5}]$, which is obtained by a typical example of the synthesis method of the present invention, that is, by mixing the above nitrobenzene solution of tpt with the above methanol solution of $ZnI_2$ and stirring the mixture at room temperature, is synthesized in the reaction condition of 30 seconds at room temperature. Accordingly, $[(ZnI_2)_3(tpt)_2(PhNO_2)_{5.5}]$ can be said to be a kinetically-controlled product. Therefore, it is possible to synthesize a kinetically-stable polymer complex by designing or setting, for example, the reaction condition of the polymer complex from a kinetic standpoint.

Also in the present invention, it is considered that channels of the polymer complex are formed by a template effect caused by the solvent B which dissolves the tridentate ligand in the ligand solution (2). More specifically, it is considered that when forming the polymer complex, the solvent which can cause a strong interaction with the tridentate ligand goes into the polymer complex because of its interaction and forms a space inside the polymer complex. Then, even if the template solvent is removed by guest exchange after the formation of the polymer complex, the channels are maintained.

Therefore, it is possible to precisely control the shape, size, etc. of the channels by selecting not only the metal species and multidentate ligand which forms the three-dimensional structure of the polymer complex, but also the solvent B which dissolves the multidentate ligand.

As described above, according to the synthesis method of the present invention, it is possible to synthesize a polymer complex having channels in a short time. Although the time required for the synthesis of the polymer complex varies depending on the amount of the metallic solution (1) and ligand solution (2) to be mixed, the mixing method, the shape of a reaction container, the reaction temperature, etc., according to the present invention, it is possible to synthesize a polymer complex in a second-scale mixing time within one minute to bring the metallic solution (1) into contact with the ligand solution (2) thereby producing a microcrystal.

Because the resulting polymer complex is a single component, it is possible to synthesis a polymer complex selectively and in bulk quantity. Moreover, it is possible to precisely control the shape, size, etc. of the channels of the resulting polymer complex by appropriately selecting, as aforementioned, the metal species, the ligand and the solvent which can dissolve them.

Also, because the resulting polymer complex is powdery microcrystals, it can be expected to be used as a microporous material which has a large surface area and shows quick absorption performance.

Hereinafter, the synthesis method of the present invention will be explained in detail.

In the present invention, the zinc halide is coordinated with a plurality of tridentate ligands to form a three-dimensional coordination network. Thus, the zinc halide serves as a clasp to connect the tridentate ligands. As the metal species which can serve as such a clasp, there may be mentioned one which can form a coordination bond with a different atom at each vertex of the regular tetrahedron, that is, one which can form a tetrahedral coordination bond.

In the present invention, zinc halide (II) is used as the tetrahedral metal species. In particular, there may be mentioned zinc bromide ($ZnBr_2$) and zinc iodide ($ZnI_2$).

As the solvent A which dissolves the zinc halide, one may be used and is not particularly limited as long as it can dissolve the zinc halide which is a metal species serving as a clasp. Preferred are alcohols which do not form a strong coordination bond with a metal, such as methanol, ethanol, isopropyl alcohol and tert-butyl alcohol. The solvent A may be one solvent alone, or a mixture of two or more kinds of solvents.

The metallic solution (1), which is a mixture of the zinc halide (II) with the solvent A, can be obtained by mixing and stirring the zinc halide (II) and the solvent A by any method to dissolve the zinc halide in the solvent A. As the method of mixing and stirring, it is only required to adopt the type or mixing ratio of the metal species and tridentate ligand to the composition ratio of a polymer complex to be produced, and one may be used and is not particularly limited as long as it can uniformly dissolve the zinc halide in the solvent A.

As the tridentate ligand coordinated to the zinc of the zinc halide (II), one may be used and is not particularly limited as long as it has three coordination sites which can form a coordination bond with the zinc of the zinc halide. Multidentate ligands having four or more coordination sites can form a polymer complex having a three-dimensional coordination network; however, tridentate ligands are more likely to form a kinetically-controlled reaction product.

The directions of coordination bonds formed by the three coordination sites of the tridentate ligand are preferably present in almost the same plane. This is because, as in this case, a regular three-dimensional coordination network can be formed when the vectors of the coordination bonds formed by the coordination sites are present in the same plane.

From the viewpoint of capability to form a regular three-dimensional coordination network, preferred is a tridentate ligand having a structure in which the three coordination sites thereof are arranged radially from the center of the tridentate ligand at regular intervals. Particularly preferred is a tridentate ligand having a structure in which three coordination sites thereof are arranged radially from the center of the tridentate ligand at regular intervals in almost the same plane.

It is to be noted that the term "almost the same plane" used herein refers to not only the state in which the coordination sites are present in the completely same plane, but also the state in which the coordination sites are present in a plane which is slightly off, for example, in a plane which intersects at an angle of 20° or less with a plane that serves as the standard. The center of the tridentate ligand refers to the center position which is observed when looking at the tridentate ligand two-dimensionally. The state in which the three coordination sites are arranged radially from the center at regular intervals refers to a state in which the three coordination sites are each arranged on a line which extends radially from the center at regular intervals.

Specific examples of the tridentate ligand include an aromatic compound represented by the following Formula (1):

$$Ar\text{-}(X\text{---}Y)_3 \qquad \text{Formula 1}$$

wherein Ar is a structure having an aromatic ring; X is a divalent organic group or a single bond through which Ar and Y are directly bound to each other; Y is a coordinating atom or a coordinating atom-containing atomic group; and a plurality of Xs contained in one molecule may be different from one another, and a plurality of Ys may be different from one another.

In Formula 1, Ar has a π plane forming a pseudo-plane structure. Ar is not particularly limited and may be appropriately selected by considering a certain influence of the molecular size of the tridentate ligand on the size of a channel to be formed in the polymer complex. Specific examples of Ar include a monocyclic aromatic ring, particularly a 6-membered aromatic ring or a condensed polycyclic aromatic ring bi- to pentacyclic, particularly a condensed polycyclic aromatic ring having two to five 6-membered aromatic rings condensed therein.

For easiness in synthesis, Ar is preferably a monocyclic aromatic ring such as a 6-membered aromatic ring. Examples of the monocyclic 6-membered aromatic ring include a benzene ring, a triazine ring, a pyridine ring, a pyrazine ring, etc.

Ar may be a structure having an aromatic ring, and may partially contain an alicyclic cyclic structure or an endocyclic heteroatom. Ar may have a substituent other than —(X—Y).

When X intermediating between Ar and Y in Formula 1 is a divalent organic group, its chain length etc. may be selected appropriately depending on the required size etc. of a channel formed in the polymer complex. For forming a channel that can incorporate an organic compound having a relatively large molecular size, examples of X include a divalent aliphatic group having 2 to 6 carbon atoms, a 6-membered divalent monocyclic aromatic ring, and a condensed polycyclic aromatic ring having two to four 6-membered aromatic rings condensed therein.

The aromatic ring may contain an endocyclic hetero atom or may have a substituent. The aromatic ring may partially contain an alicyclic structure. The alicyclic group may have a branched structure, may contain an unsaturated bond, or may contain a hetero atom.

Specific examples of the divalent organic group include a monocyclic aromatic ring such as a phenylene group, thiophenylene, or furanylene, a condensed polycyclic aromatic ring having benzene rings condensed therein, such as a naphthyl group or anthracene, an aliphatic group such as an acetylene group, an ethylene group, an amido group or an ester group, and a group wherein these groups, the number of which is arbitrary, are linked to one another in an arbitrary order. A plurality of Xs contained in one molecule may be the same or different from one another, but is usually preferably the same from the viewpoint of easy synthesis.

Y is a coordinating atom having a coordination site which can be coordinated to the zinc ion of the zinc halide, or an atomic group containing such a coordinating atom, and is not particularly limited as long as it can be coordinated to the zinc to form a three-dimensional coordination network. Examples of Y include groups represented by the following Formula 2:

Formula 2

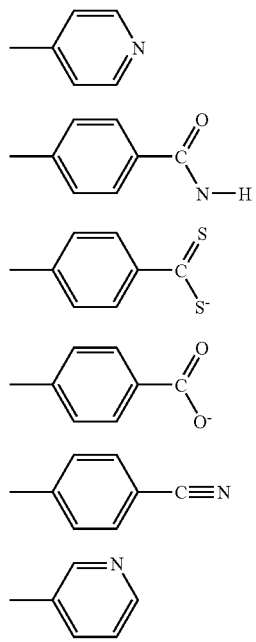

Formulae 2 (b), 2 (c) and 2 (d) have a resonance structure so that a lone electron pair can be given to the central metal ion. Hereinafter, the resonance structure of Formula 2 (c) is shown as a typical example.

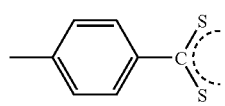

Y may be a coordinating atom itself having a coordination site, or may be an atomic group containing a coordinating atom having a coordination site. For example, the above-mentioned 4-pyridyl group (2 (a)) is an atomic group containing a coordinating atom (N). From the viewpoint of attaining suitable coordination strength upon coordination bonding to the zinc ion via a lone electron pair possessed by the coordinating atom of Y, the pyridyl group (2 (a), 2 (f)) is particularly preferable among the groups of the above formulae.

The tridentate ligand is preferably an aromatic compound wherein all coordination sites of the tridentate ligand exist in almost the same plane. Particularly, the aromatic compound ligand when viewed as a whole is preferably in the form of a pseudo-plane owing to its π-conjugated system. That is, all Ys contained in the tridentate ligand (1) represented by Formula 1 above are preferably present in almost the same plane. It is particularly preferable that three —(X—Y)s bound to and Ar become unified by the π-conjugated system to form a stable pseudo-plane structure in which all Ys exist.

From the viewpoint of allowing the polymer complex to form a strong three-dimensional structure, it is preferable that in the tridentate ligand wherein Ar and three —(X—Y)s become unified by the π-conjugated system to form a pseudo-plane structure, —(X—Y) has a rigid linear structure, and in an environment intended to be used, its rotation on the axis is restricted.

From this viewpoint, preferable examples of X among those mentioned above include a single bond through which Ar and Y are directly bound to each other, an aromatic group, for example a monocyclic aromatic ring such as a phenylene group or a condensed polycyclic aromatic ring such as a naphthyl group or anthracene, an aliphatic group such as an acetylene group or an ethylene group, and a group wherein these groups, the number of which is arbitrary, are linked to one another in an arbitrary order. When —(X—Y) has a structure composed of an aromatic ring, an acetylene group or an ethylene group or a structure having these groups linked therein, its axial rotation is restricted due to steric hindrance. When the structure composed of an aromatic ring, an acetylene group or an ethylene group forms a conjugated system where π electrons are delocalized, its axial rotation is restricted by an energy barrier of the conformation. Accordingly, the tridentate ligands represented by Formula 1 can become unified to attain a pseudo-plane structure, thereby forming a stable three-dimensional coordination network.

From the viewpoint of ease in design of the polymer complex, Y preferably has a coordination site, particularly a lone electron pair in the extending direction of the axis of —(X—Y) having the rigid linear structure described above. More preferably, the directions of coordination bonds formed respectively by these coordination sites are present in almost the same plane.

As the above-mentioned tridentate ligand having the structure wherein coordination sites are arranged radially at regular intervals in the extending direction of a plane formed by the π-conjugated system of the aromatic ring with the aromatic ring-containing structure Ar as the center, and in which the directions of coordination bonds formed by three Ys each having a coordination site are present in almost the same plane, there may be mentioned 2,4,6-tris-(4-pyridyl)-1,3,5-triazine (tpt) represented by the following Formula 4:

Formula 4

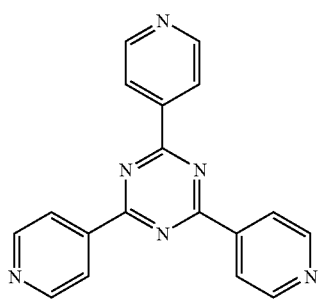

As the solvent B which dissolves the tridentate ligand, one may be used and is not particularly limited as long as it can dissolve the tridentate ligand. Particularly in the case where an interaction occurs between the solvent B and the tridentate ligand, the solvent B is considered to serve as a mold of the channels of the polymer complex. The size, shape, etc., of the channels to be formed is considered to vary depending on the solvent B used, so that it is preferable to select the solvent B considering the interaction with the tridentate ligand, molecular size, polarity, etc.

As the solvent B, there may be mentioned an aromatic compound. Because the tridentate ligand represented by the above (1), tpt or the like has an aromatic ring, the interaction between the tridentate ligand and the solvent B can be enhanced by using an aromatic compound as the solvent B, and thus it becomes possible to form regular channels certainly. Specific examples thereof include nitrobenzene, benzene, toluene, etc. The solvent B may be one kind alone or a mixture of two or more kinds.

The ligand solution (2), which is a mixture of the tridentate ligand with the solvent B, can be obtained by mixing and stirring the tridentate ligand and the solvent B by any method to dissolve the tridentate ligand compound in the solvent B. As the method of mixing and stirring, it is only required to adopt the type or mixing ratio of the metal species and tridentate ligand to the composition ratio of a polymer complex to be produced, and one may be used and is not particularly limited as long as it can uniformly dissolve the tridentate ligand in the solvent B.

For the purpose of concentration regulation to prevent the metal species or tridentate ligand from being precipitated alone in the early stage of mixing, the ligand solution (2) may also contain the solvent A which can dissolve metal species besides the solvent B. The content of the solvent A is preferably 20 vol % or less with respect to the solvent B.

By instantly mixing the thus-obtained metallic solution (1) and ligand solution (2) to be a single-phase solution, a microcrystal of a polymer complex having a three-dimensional coordination network can be formed, in which network the tridentate ligand in the ligand solution (2) is coordinated to the zinc of the zinc halide in the metallic solution (1), and three-dimensionally and regularly arranged channels are formed.

The method of mixing and stirring the metallic solution (1) and the ligand solution (2) is not particularly limited as long as a single-phase solution can be obtained by the method in a short time, and any method can be employed depending on the amount of synthesis, the shape of a reaction container, the reaction temperature, etc. For example, the total amount of the metallic solution (1) and the total amount of the ligand solution (2) may be mixed together at once and stirred, or mixing and stirring may be performed while the metallic solution (1) and the ligand solution (2) are continuously supplied. Alternatively, the metallic solution (1) may be divided into several lots and supplied to the ligand solution (2) to be mixed and stirred without deteriorating the effect of the present invention, vice versa.

The condition applied to the step of mixing the metallic solution (1) with the ligand solution (2) is not particularly limited. For example, the reaction may be performed under a mild condition of room temperature (about 10 to 30° C.).

In the manner as described above, according to the present invention, it is possible to obtain a polymer complex in the form of powdery microcrystals by taking very simple steps and also in a short time. Furthermore, as described above, it is possible to obtain a single-component polymer complex and, according to the synthesis method of the present invention, it is possible to obtain a polymer complex very efficiently.

As the method of analyzing the structure of a microcrystalline powder obtained by the synthesis method of the present invention, there may be mentioned elemental analysis, thermogravimetry-mass spectrometry (TG-MS), powder X-ray crystal structure analysis, etc. By using, among them, powder X-ray crystal structure analysis, it has been succeeded in determining the structure of the microcrystalline powder by measuring the microcrystalline powder for its diffraction pattern with radiation, determining the structure of the microcrystalline powder from the resulting diffraction pattern with the use of DASH program, and in refining the structure by performing Rietveld analysis with the use of RIETAN-FP program.

Hereinafter, the crystal structure of polymer complex 1 $[(ZnI_2)_3(tpt)_2(PhNO_2)_{5.5}]_n$ will be described, which is a typical example of the polymer complex obtained by the synthesis method of the present invention, and is obtained by the reaction represented by Formula (5), that is, by mixing a nitrobenzene solution of tpt with a methanol solution of $ZnI_2$ at room temperature and stirring the mixture for 30 seconds (see FIG. 1).

As described above, the polymer complex 1 is isomorphic to single crystal $[(ZnI_2)_3(tpt)_2(PhNO_2)_{5.5}]_n$, which can be obtained by crystal growing with a counter diffusion method using a nitrobenzene solution of tpt and a methanol solution of $ZnI_2$ (see FIG. 3 and Angew. Chem. Int. Ed. 2002, 41, No. 18, pp. 3392-3395). More specifically, two kinds of three-dimensional coordination networks 1a and 1b, in which Zn of $ZnI_2$ forms a tetrahedral coordination bond with two Is and two lone electron pairs of a pyridyl group of tpt and thus is three-dimensionally connected to them, are interpenetrated to form a complexed three-dimensional coordination network. The three-dimensional coordination networks 1a and 1b do not have a direct or indirect bond via which, for example, both the networks have Zn in common. The two networks are each an independent polymer skeleton and are interpenetrated and nested alternately to each other so as to have the same space in common. Then, complexes which are each formed by interpenetration of two kinds of three-dimensional coordination networks 1a and 1b, are continuously stacked, thereby forming a complexed three-dimensional coordination network.

This three-dimensional coordination network has a closed circular structure consisting of 10 tpt molecules and 10 Zn atoms as the shortest closed circular structure, and is considered to have (10,3)-b configuration. Also, along (010) axis, this three-dimensional coordination network can be regarded as a helical and hexagonal three-dimensional coordination network. A polymer complex formed by interpenetration of two such three-dimensional coordination networks has one kind of channels which penetrate these two three-dimensional coordination networks and are regularly arranged.

The crystal structure of the polymer complex obtained by the synthesis method of the present invention is not limited to the above structure.

The polymer complex provided by the present invention has a function of incorporating and/or releasing and/or transporting a guest molecule selectively. Accordingly, separation, refinement, storage, etc., of a specific component are made possible by using the polymer complex. Furthermore, as mentioned above, it is possible to control the shape, size, atmosphere of the channels by molecular design, so that the polymer complex can be expected to be effectively used for various purposes in a wide variety of fields.

EXAMPLES

Synthesis of Polymer Complex 1

In a mixture of nitrobenzene/methanol (32 ml/4 ml), tpt of 50.2 mg was dissolved to prepare a ligand solution. At room temperature, the obtained ligand solution was mixed with a metallic solution prepared by dissolving $ZnI_2$ of 76.5 mg in methanol of 8 ml, followed by stirring for 30 seconds, thereby obtaining a white powder of 151.7 mg (yield: 81.6%).

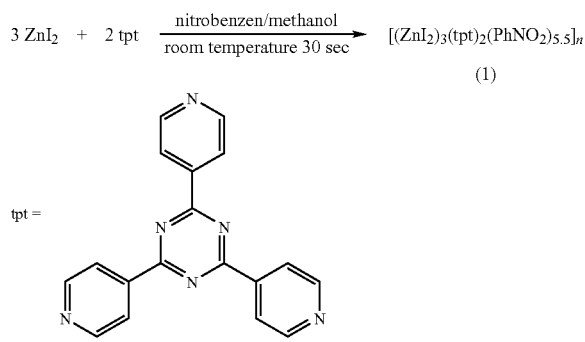

(Formula 5)

$$3 ZnI_2 + 2 tpt \xrightarrow[\text{room temperature 30 sec}]{\text{nitrobenzen/methanol}} [(ZnI_2)_3(tpt)_2(PhNO_2)_{5.5}]_n$$

(1)

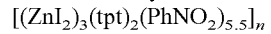

tpt =

The thus-obtained white powder sample was identified by elemental analysis and thermogravimetry-mass spectrometry (TG-MS) and found to be $[(ZnI_2)_3(tpt)_2(PhNO_2)_{5.5}]_n$ (polymer complex 1).

<Elemental Analysis Result>

$[(ZnI_2)_3(tpt)_2(PhNO_2)_{5.5}]_n$

Theoretical Values: C: 36.68%, H: 2.30%, N: 10.85%

Measured Values: C: 36.39%, H: 2.43%, N: 10.57%

Furthermore, powder X-ray crystal structure analysis with radiation synchrotron was performed on the obtained white powder sample with Spring-8 (wavelength: 0.69995(2) Å). Therefore, the white powder was found to be monoclinic with space group C2/c and to have a lattice volume of 16140 Å³ and a nested network structure (coordination network) which had channels of a single type (see FIG. 1). Despite the polymer complex had the large lattice volume and low symmetry, by using software program DASH, the skeleton structure of the polymer complex 1 could be primarily obtained from the powder X-ray diffraction data thus obtained. FIG. 1 (1A) shows the crystal structure of the polymer complex 1. FIG. 1 (1B) shows diffraction patterns of the polymer complex 1 (solid line: measured diffraction pattern, dashed line: theoretical diffraction pattern derived by simulation).

Figure 1:
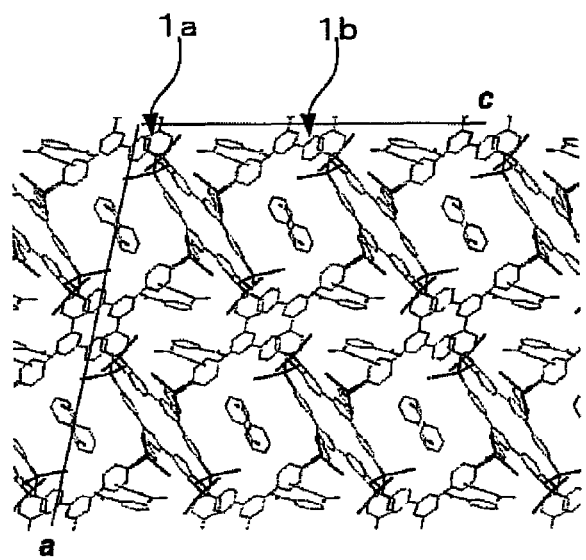
FIG. 1 shows diagrams showing the crystal structure and radiation diffraction patterns of polymer complex 1.
Figure 1:
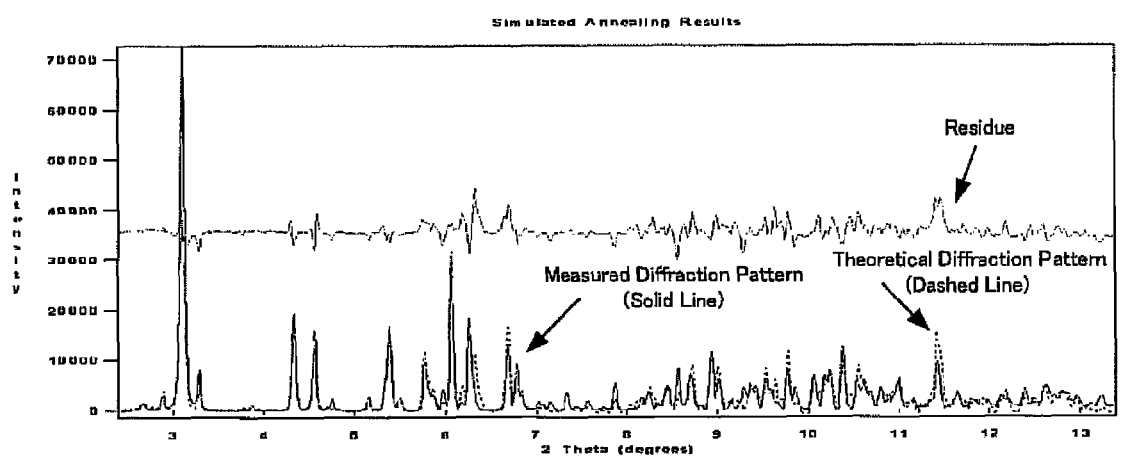

In FIG. 1 (1B), the theoretical diffraction pattern derived from the crystal structure of the polymer complex 1 by simulation and the measured diffraction pattern showed a good concordance therebetween, and the residue which corresponds to the difference between the diffraction patterns was small.

On the other hand, nitrobenzene of 4 ml and methanol of 1 ml were charged into a test tube, and tpt of 6.3 mg was dissolved therein. Then, a solution prepared by dissolving $ZnI_2$ of 9.6 mg in methanol of 1 ml was gently added thereto to form a top layer and left at about 15 to 25° C. (room temperature) for about seven days, thereby obtaining polymer complex 1' $[(ZnI_2)_3(tpt)_2(PhNO_2)_{5.5}]_n$.

The result of X-ray crystal structure analysis of the thus-obtained polymer complex 1' is shown in FIG. 3. No guest molecule is shown in FIG. 3 because it is omitted.

As a result of comparing the above-obtained crystal structure of the polymer complex 1 (FIG. 1 (1A)) to that of the polymer complex 1' (FIG. 3 (3A)), it is clear that their three-dimensional structures are identical.

Synthesis of Polymer Complex 2

In a mixture of nitrobenzene/methanol (32 ml/4 ml), tpt of 50.2 mg was dissolved to prepare a ligand solution. At room temperature, the obtained ligand solution was mixed with a metallic solution prepared by dissolving $ZnBr_2$ of 54.0 mg in methanol of 8 ml, followed by stirring for 30 seconds, thereby obtaining a white powder of 77.3 mg (yield: 47.8%).

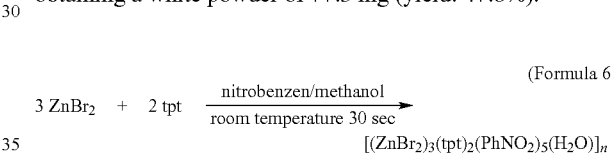

(Formula 6)

$$3 ZnBr_2 + 2 tpt \xrightarrow[\text{room temperature 30 sec}]{\text{nitrobenzen/methanol}}$$

$$[(ZnBr_2)_3(tpt)_2(PhNO_2)_5(H_2O)]_n$$

(2)

The thus-obtained white powder sample was identified by elemental analysis and thermogravimetry-mass spectrometry (TG-MS) and found to be $[(ZnBr_2)_3(tpt)_2(PhNO_2)_5(H_2O)]_n$ (polymer complex 2).

<Elemental Analysis Result>

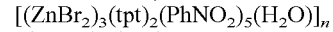

$[(ZnBr_2)_3(tpt)_2(PhNO_2)_5(H_2O)]_n$

Theoretical Values: C: 40.99%, H: 2.66%, N: 12.31%

Measured Values: C: 40.96%, H: 2.83%, N: 12.08%

Figure 2:
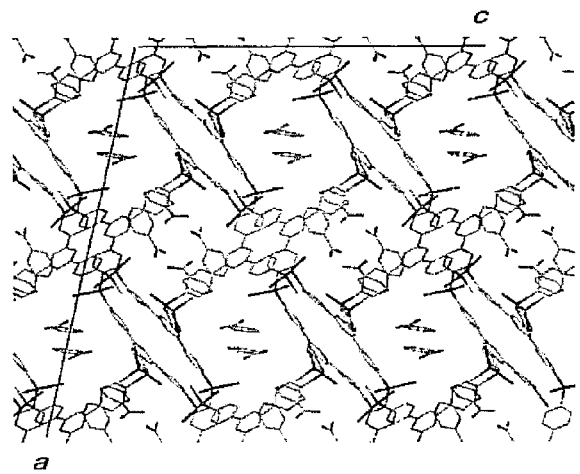
FIG. 2 shows diagrams showing the crystal structure and radiation diffraction patterns of polymer complex 2.
Figure 2:
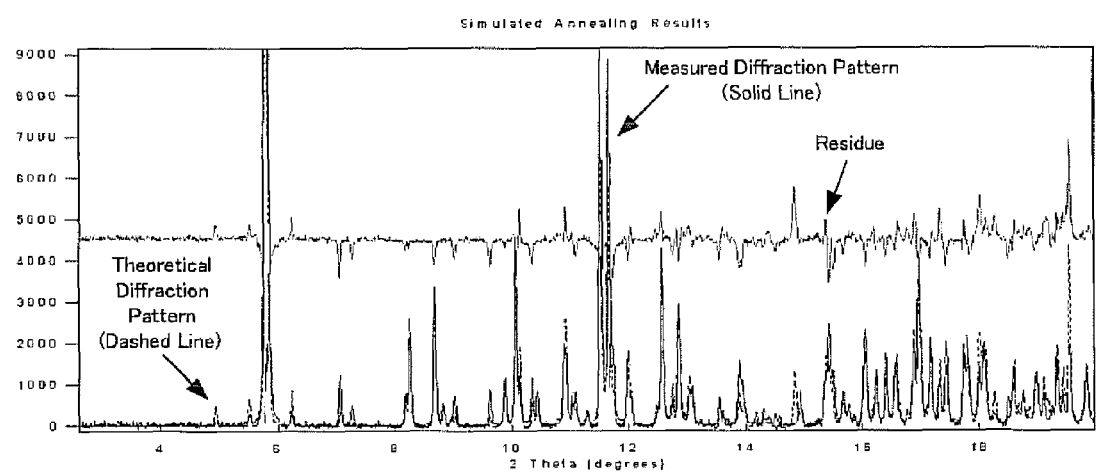

Furthermore, powder X-ray crystal structure analysis with radiation synchrotron was performed on the obtained white powder sample with Spring-8 (wavelength: 1.29918(3) Å). Therefore, the white powder was found to be monoclinic with space group C2/c and to have a lattice volume of 15638 Å³ and a nested network structure (coordination network) which had channels of a single type (see FIG. 2). Despite the polymer complex 2 had the large lattice volume and low symmetry, by using software program DASH, the skeleton structure of the polymer complex 2 could be primarily obtained from the powder X-ray diffraction data thus obtained. FIG. 2 (2A) shows the crystal structure of the polymer complex 2. FIG. 2 (2B) shows diffraction patterns of the polymer complex 2 (solid line: measured diffraction pattern, dashed line: theoretical diffraction pattern derived by simulation).

In FIG. 2 (2B), the theoretical diffraction pattern derived from the crystal structure of the polymer complex 2 by simulation and the measured diffraction pattern showed a good concordance therebetween, and the residue which corresponds to the difference between the diffraction patterns was small.

As a result of the model calculations performed on the presumption that the three-dimensional structure of the polymer complex 2 was similar to the structure of the polymer complex 1 obtained by the X-ray crystal structure analysis, the theoretical diffraction pattern thus obtained was almost identical with the actually measured diffraction pattern obtained in the powder X-ray crystal structure analysis, and there was almost no residue left which corresponds to the difference between the diffraction patterns. Therefore, the polymer complex 1 and the polymer complex 2 are considered to have three-dimensional coordination networks which are isomorphic to each other.

The invention claimed is:

1. A synthesis method of a polymer complex crystal wherein (1) a metallic solution, which is a mixture of zinc halide(II) and a solvent A that can dissolve the zinc halide, is mixed with (2) a ligand solution, which is a mixture of 2,4,6-tris-(4-pyridyl)-1,3,5-triazine and a solvent B that can dissolve the 2,4,6-tris-(4-pyridyl)-1,3,5-triazine, to be a single-phase solution, thereby synthesizing a microcrystal of a polymer complex having a three-dimensional coordination network formed by coordinating the 2,4,6-tris-(4-pyridyl)-1,3,5-triazine to zinc of the zinc halide and having channels that are three-dimensionally and regularly arranged in the three-dimensional coordination network.

2. The synthesis method of a polymer complex crystal according to claim 1, wherein the step of mixing the metallic solution with the ligand solution is performed at room temperature.

3. The synthesis method of a polymer complex crystal according to claim 1, wherein the zinc halide(II) is zinc bromide(II) or zinc iodide(II).

4. The synthesis method of a polymer complex crystal according to claim 1, wherein the solvent B is an aromatic compound.

5. The synthesis method of a polymer complex crystal according to claim 4, wherein the solvent B is nitrobenzene.

6. The synthesis method of a polymer complex crystal according to claim 1, wherein the solvent A is 20 vol % or less with respect to the solvent B.

* * * * *

UNITED STATES PATENT AND TRADEMARK OFFICE
CERTIFICATE OF CORRECTION

PATENT NO. : 8,288,535 B2  
APPLICATION NO. : 12/530240  
DATED : October 16, 2012  
INVENTOR(S) : Makoto Fujita et al.

Page 1 of 1

It is certified that error appears in the above-identified patent and that said Letters Patent is hereby corrected as shown below:

In the Specification

Col. 1, line 24: replace "trans it ion" with --transition--.

Signed and Sealed this  
Eighth Day of April, 2014

Michelle K. Lee  
*Deputy Director of the United States Patent and Trademark Office*